United States Patent
Sloman et al.

(10) Patent No.: US 6,345,201 B1
(45) Date of Patent: Feb. 5, 2002

(54) SYSTEM AND METHOD FOR VENTRICULAR CAPTURE USING FAR-FIELD EVOKED RESPONSE

(75) Inventors: Laurence S. Sloman, West Hollywood; Kerry A. Bradley, Glendale, both of CA (US)

(73) Assignee: Pacesetter, Inc., Sylmar, CA (US)

(*) Notice: Subject to any disclaimer, the term of this patent is extended or adjusted under 35 U.S.C. 154(b) by 0 days.

(21) Appl. No.: 09/460,614

(22) Filed: Dec. 14, 1999

Related U.S. Application Data

(63) Continuation-in-part of application No. 09/124,811, filed on Jul. 29, 1998, now Pat. No. 6,101,416.

(51) Int. Cl.$^7$ .............................................. A61N 1/368
(52) U.S. Cl. ................................ 607/28; 607/4; 607/9; 600/521
(58) Field of Search ............................... 607/28, 27, 9, 607/4, 5; 600/509, 521

(56) References Cited

U.S. PATENT DOCUMENTS

| | | | | |
|---|---|---|---|---|
| 5,111,811 A | * | 5/1992 | Smits | 128/419 |
| 5,269,319 A | * | 12/1993 | Schulte et al. | 128/786 |
| 5,331,966 A | * | 7/1994 | Bennett et al. | 128/696 |
| 5,534,022 A | * | 7/1996 | Hoffmann et al. | 607/122 |
| 5,571,144 A | * | 11/1996 | Schroeppel | 607/28 |
| 5,683,426 A | * | 11/1997 | Greenhut et al. | 607/9 |
| 5,755,739 A | * | 5/1998 | Sun et al. | 607/14 |
| 5,766,225 A | * | 6/1998 | Kramm | 607/4 |
| 6,169,921 B1 | * | 1/2001 | KenKnight et al. | 607/4 |

* cited by examiner

*Primary Examiner*—Kennedy Schaetzle

(57) ABSTRACT

An implantable pacemaker delivers a stimulation pulse in the ventricular chamber of patient's heart and automatically verifies ventricular capture. A control system of the pacemaker sets a far-field interval window after a predetermined delay period from the delivery of the stimulation pulse, for verifying ventricular capture. The far-field interval window is approximately 100 msec, and provides an opportunity for the control system to sense the far-field signal that occurs in response to the stimulation pulse. The delivery of the stimulation pulse also initiates a post ventricular atrial blanking period on an atrial channel, and the far-field interval window is initiated during the post ventricular atrial blanking period.

30 Claims, 6 Drawing Sheets

SYSTEM AND METHOD FOR VENTRICULAR CAPTURE USING FAR-FIELD EVOKED RESPONSE

This application is a continuation-in-part application of U.S. application Ser. No. 09/124,811, filed Jul. 29, 1998, now U.S. Pat. No. 6,101, 416, which is incorporated herein by reference in its entirety.

FIELD OF THE INVENTION

The present invention relates in general to cardiac stimulation devices, such as pacemakers, defibrillators, cardioverters, implantable cardioverter-defibrillators ("ICDs"), and similar cardiac stimulation devices that are capable of monitoring and detecting electrical activities and events within the heart. In particular, this invention pertains to a system and method for automating the detection of capture on a ventricular channel of an implantable dual-chamber stimulation device, using far-field evoked response sensed on an atrial channel.

BACKGROUND OF THE INVENTION

Implantable medical devices, such as pacemakers, defibrillators, cardioverters, and implantable cardioverter-defibrillators ("ICDs"), collectively referred to herein as implantable cardiac stimulating devices, are designed to monitor and stimulate the heart of a patient who suffers from a cardiac arrhythmia. Using leads connected to a patient's heart, these devices typically stimulate the cardiac muscles by delivering electrical pulses in response to measured cardiac events that are indicative of a cardiac arrhythmia. Properly administered therapeutic electrical pulses often successfully reestablish or maintain the heart's regular rhythm.

Implantable cardiac stimulating devices can treat a wide range of cardiac arrhythmias by using a series of adjustable parameters to alter the energy, shape, location, and frequency of the therapeutic pulses. The adjustable parameters are usually defined in a computer program stored in a memory of the implantable device. The program, which is responsible for the operation of the implantable device, can be defined or altered telemetrically by a medical practitioner using an external implantable device programmer.

Programmable pacemakers are generally of two types: (1) single-chamber pacemakers, and (2) dual-chamber pacemakers. In a single-chamber pacemaker, the pacemaker provides stimulation pulses to, and senses cardiac activity within, a single-chamber of the heart, either the right ventricle or the right atrium. In a dual-chamber pacemaker, the pacemaker provides stimulation pulses to, and senses cardiac activity within, two chambers of the heart, namely both the right atrium and the right ventricle. The left atrium and left ventricle can also be sensed and paced, provided that suitable electrical contacts are effected therewith.

Pacemakers also have a great number of adjustable parameters that must be tailored to a particular patient's therapeutic needs. One adjustable parameter of particular importance in pacemakers is the pacemaker's stimulation energy. For the pacemaker to perform its intended function, it is critically important that the delivered electrical stimuli be of sufficient energy to depolarize the cardiac tissue, a condition known as "capture".

When a pacemaker stimulation pulse stimulates either the atrium or the ventricle during an appropriate portion of a cardiac cycle, it is desirable to have the heart properly respond to the stimulus provided. Every patient has a "capture threshold" which is generally defined as the minimum amount of stimulation energy necessary to effect capture. Capture should preferably be achieved at the lowest possible energy setting yet provide enough of a safety margin so that, if a patient's threshold increase, the output of an implantable pacemaker, i.e. the stimulation energy, will still be sufficient to maintain capture. Dual-chamber pacemakers may have differing atrial and ventricular stimulation energy that correspond to atrial and ventricular capture thresholds, respectively.

Earlier pacemakers had a predetermined and unchangeable stimulation energy, which proved to be problematic because the capture threshold is not a static value and may be affected by a variety of physiological and other factors. For example, certain cardiac medications may temporarily raise or lower the threshold from its normal value. In another example, fibrous tissue that forms around pacemaker lead heads within several months after implantation may raise the capture threshold.

As a result, some patients may eventually suffer from loss of capture, as their pacemakers were unable to adjust the pre-set stimulation energy to match the changed capture thresholds. One attempted solution was to set the level of stimulation pulses fairly high so as to avoid loss of capture due to a change in the capture threshold. However, this approach may result in some discomfort to patients who were forced to endure unnecessarily high levels of cardiac stimulation. Furthermore, such stimulation pulses would consume extra battery resources, thus shortening the useful life of the pacemaker.

When programmable pacemakers were developed, the stimulation energy was implemented as an adjustable parameter that could be set or changed by a medical practitioner. Typically, such adjustments were effected by the medical practitioner using an external programmer capable of communication with an implanted pacemaker via a magnet applied to a patient's chest or via telemetry. The particular setting for the pacemaker's stimulation energy was usually derived from the results of extensive physiological tests performed by the medical practitioner to determine the patient's capture threshold, from the patient's medical history, and from a listing of the patient's medications. While the adjustable pacing energy feature proved to be superior to the previously known fixed energy, some significant problems remained unsolved. In particular, when a patient's capture threshold changed, the patient was forced to visit the medical practitioner to adjust the pacing energy accordingly.

To address this pressing problem, pacemaker manufacturers have developed advanced pacemakers that are capable of determining a patient's capture threshold and automatically adjusting the stimulation pulses to a level just above that which is needed to maintain capture. This approach, called "autocapture", improves the patient's comfort, reduces the necessity of unscheduled visits to the medical practitioner, and greatly increases the pacemakers battery life by conserving the energy used to generate stimulation pulses.

However, many of these advanced pacemakers require additional circuitry and/or special sensors that must be dedicated to capture verification. This requirement increases the complexity of the pacemaker system and reduces the precious space available within a pacemaker's casing, and also increases the pacemaker's cost. As a result, pacemaker manufacturers have attempted to develop automatic capture verification techniques that may be implemented in a typical programmable pacemaker without requiring additional circuitry or special dedicated sensors.

A common technique used to determine whether capture has been effected is monitoring the patient's cardiac activity and searching for the presence of an "evoked response" following a stimulation pulse. The evoked response is the response of the heart to the application of a stimulation pulse. The patient's heart activity is typically monitored by the pacemaker by keeping track of the stimulation pulses delivered to the heart and examining, through the leads connected to the heart, electrical signals that are manifest concurrent with depolarization or contraction of muscle tissue (myocardial tissue) of the heart. The contraction of atrial muscle tissue is evidenced by generation of a P-wave, while the contraction of ventricular muscle tissue is evidenced by generation of an R-wave (sometimes referred to as the "QRS" complex). When capture occurs, the evoked response is an intracardiac P-wave or R-wave that indicates contraction of the respective cardiac tissue in response to the applied stimulation pulse. For example, using such an evoked response technique, if a stimulation pulse is applied to the ventricle (hereinafter referred to as an V-pulse), a response sensed by ventricular sensing circuits of the pacemaker immediately following the application of the V-pulse is presumed to be an evoked response that evidences capture of the ventricle.

However, it is for several reasons very difficult to detect a true evoked response. First, because the ventricular evoked response is a relatively small signal, it may be obscured by a high energy V-pulse and therefore difficult to detect and identify. Second, the signal sensed by the pacemaker's sensing circuitry immediately following the application of a stimulation pulse may be not an evoked response but noise, such as electrical noise caused, for example, by electromagnetic interference, or myocardial noise caused by random myocardial or other muscle contraction.

Another signal that interferes with the detection of an evoked response, and potentially the most difficult for which to compensate because it is usually present in varying degrees, is lead polarization. A lead/tissue interface is that point at which an electrode of the pacemaker lead contacts the cardiac tissue. Lead polarization is commonly caused by electrochemical reactions that occur at the lead/tissue interface due to application of an electrical stimulation pulse, such as a V-pulse, across the interface.

Because the evoked response is sensed through the same lead electrodes through which the stimulation pulses are delivered, the resulting polarization signal, also referred to as an "afterpotential", formed at the electrode can corrupt the evoked response that is sensed by the sensing circuits. This undesirable situation occurs often because the polarization signal can be three or more orders of magnitude greater than the evoked response. Furthermore, the lead polarization signal is not easily characterized; it is a complex function of the lead materials, lead geometry, tissue impedance, stimulation energy and other variables, many of which are continually changing over time.

In each of the above cases, the result may be a false positive detection of an evoked response. Such an error leads to a false capture indication, which in turn, leads to missed heartbeats, a highly undesirable and potentially life-threatening situation. Another problem results from a failure by the pacemaker to detect an evoked response that has actually occurred. In that case, a loss of capture is indicated when capture is in fact present, also an undesirable situation that will cause the pacemaker to unnecessarily invoke the pacing energy determination function in a chamber of the heart.

Automatic pacing energy determination is only invoked by the pacemaker when loss of ventricular capture is detected. An exemplary automatic ventricular pacing energy determination procedure has been performed as follows. When loss of ventricular capture is detected, the pacemaker increases the V-pulse output level to a relatively high predetermined testing level at which capture is certain to occur, and thereafter decrements the output level until ventricular capture is lost. The ventricular pacing energy is then set to a level slightly above the lowest output level at which ventricular capture was attained. Thus, ventricular capture verification is of utmost importance in proper determination of the ventricular pacing energy.

When a ventricular stimulation pulse is properly captured in the ventricle, a subsequent ventricular contraction results in a far-field evoked response which may be sensed through an atrial lead, as a "far-field" signal, also referred to herein as "far-field R-wave" or FFR. The far-field R-wave confirms successful ventricular capture because the ventricular contraction only occurs after a properly captured ventricular stimulation pulse.

However, previously known dual-chamber pacemakers do not sense ventricular activity through the atrial lead for a particular interval of time (i.e., the "refractory" period) subsequent to the delivery of the ventricular stimulation pulse. Furthermore, the polarization signal formed at the ventricular lead electrode may obscure and/or distort the evoked response signal, even if it were sensed.

It would thus be desirable to provide a system and method for automating the detection of capture on a ventricular channel of an implantable dual chamber stimulation device, with increased accuracy. It would also be desirable to provide a system and method for reducing the negative effect of polarization and noise on capture verification. It would further be desirable to enable the pacemaker to perform ventricular capture verification without requiring dedicated circuitry and/or special sensors.

SUMMARY OF THE INVENTION

One feature of the present invention is to address the disadvantages and limitations discussed above. In accordance with this invention, a system and method are provided for automating the detection of capture on a ventricular channel of an implantable dual chamber stimulation device, using far-field evoked response that follows a successfully captured ventricular stimulation pulse, and which is sensed on an atrial channel.

The system and method of the present invention compensate for effects of polarization and noise on the far-field R-wave (FFR) and do not require the use of special dedicated circuitry or special sensors to implement the automated procedure.

The present invention provides an implantable medical device (hereinafter "pacemaker") equipped with cardiac data acquisition capabilities. A preferred embodiment of the pacemaker of the present invention includes a control system for controlling the operation of the pacemaker, a set of leads for receiving atrial and ventricular signals and for delivering atrial and ventricular stimulation pulses, a set of sensing circuits comprised of sense amplifiers for sensing and amplifying the atrial and ventricular signals, a sampler, such as an A/D converter, for sampling atrial and/or ventricular signals, and pulse generators for generating the atrial and ventricular stimulation pulses. In addition, the pacemaker includes memory for storing operational parameters for the control system, such as atrial or ventricular signal sampling parameters, and atrial or ventricular signal samples. The pacemaker also includes a telemetry circuit for communicating with an external programmer.

In a preferred embodiment, the pacemaker control system periodically performs a ventricular capture verification test and, when necessary, a ventricular pacing threshold assessment test, which performs an assessment of the stimulation energy in the ventricular chamber of the patient's heart. The frequency with which these tests are performed are preferably programmable parameters set by the medical practitioner using an external programmer when the patient is examined during an office visit or remotely via a telecommunication link. The appropriate testing frequency parameter will vary from patient to patient and depend on a number of physiologic and other factors. For example, if a patient is on a cardiac medication regimen, the patient's ventricular capture threshold may fluctuate, thus requiring relatively frequent testing and adjustment of the atrial stimulation energy. Preferably the system and method of the present invention are implemented in a dual-chamber pacemaker.

In one embodiment of the invention, the pacemaker delivers a ventricular stimulation pulse and then samples a resulting far-field R-wave ("FFR") of the evoked response on the atrial channel during a predetermined far-field interval ("FFI") window. The FFI window starts a short time (e.g. ranges between 10 ms and 50 ms) after the ventricular pulse is initiated and continues for a predetermined period (e.g. ranges between 50 ms and 125 ms).

The pacemaker then compares the FFR sample to a predetermined far-field signal recognition template to verify whether the FFR sample morphology corresponds to a far-field R-wave that is expected to follow a successfully captured ventricular stimulation pulse. If the FFR sample is approximately equal to the far-field signal recognition template, then ventricular capture is deemed verified. Otherwise, the pacemaker performs a ventricular stimulation energy determination procedure. The far-field interval window and the far-field signal recognition template may be predefined by the medical practitioner and stored in the pacemaker memory.

According to one embodiment of the present invention, a control system of the pacemaker sets the far-field interval window to approximately 100 msec. The delivery of the stimulation pulse initiates a post ventricular atrial blanking period on the atrial channel, and the far-field interval window is initiated during the post ventricular atrial blanking period.

The system and method of the present invention thus automatically verify ventricular capture and, when necessary, automatically determine a proper ventricular stimulation energy of the patient's pacemaker, without requiring dedicated or special circuitry and/or sensors. The system and method allow ventricular beat-by-beat autocapture in dual chamber pacemakers where lead characteristics could prevent reliable detection of the ventricular evoked response on the ventricular lead. In addition, the system and method enable the pacemaker to automatically choose the best method for determining ventricular capture without compromising the patient's safety, and to reduce the pacemaker energy consumption by allowing an autocapture algorithm to be executed.

BRIEF DESCRIPTION OF THE DRAWINGS

These and other features and advantages of the invention will now be described with reference to the drawings of a preferred embodiment, which is intended to illustrate and not to limit the invention, and in which like numerals refer to like parts throughout the disclosure.

DETAILED DESCRIPTION OF THE INVENTION

Figure 1:
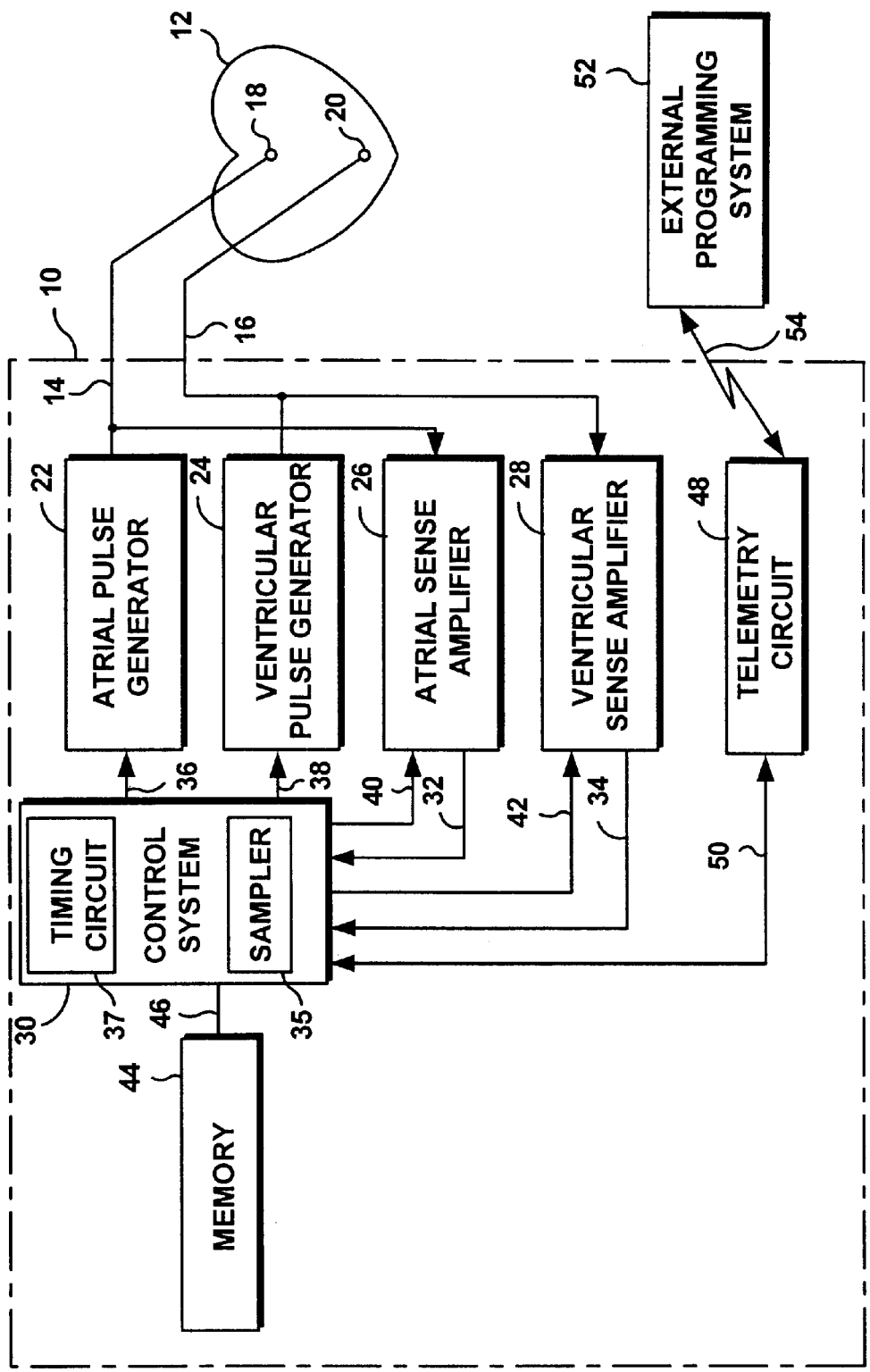
FIG. 1 is a block diagram of a dual-chamber pacemaker in accordance with the principles of the present invention.

The system and method of the present invention are intended for use in a cardiac stimulation device, such as a pacemaker, a defibrillator, a cardioverter, an implantable cardioverter-defibrillators ("ICDs"), or a similar cardiac stimulation device capable of monitoring and detecting electrical activities and events within a patient's heart 12. This cardiac stimulation device will be referred to herein as pacemaker 10, and is generally illustrated in FIG. 1.

The pacemaker 10 is coupled to a patient's heart 12 by way of leads 14 and 16. The lead 14 includes an electrode 18 which is in contact with one of the atria of the heart 12. The lead 16 includes an electrode 20 which is in contact with one of the ventricles. The lead 14 carries stimulating pulses to the electrode 18 from an atrial pulse generator 22, while the lead 16 carries stimulating pulses to the electrode 20 from a ventricular pulse generator 24. In addition, electrical signals from the atria are carried from the electrode 18, through the lead 14, to the input terminal of an atrial sense amplifier 26. Electrical signals from the ventricles are carried from the electrode 20, through the lead 16 to the input terminal of a ventricular sense amplifier 28.

Operatively controlling the dual-chamber pacemaker 10 is a control system 30. The control system 30 is preferably a microprocessor-based system such for example as that disclosed in commonly-assigned U.S. Pat. No. 4,940,052 of Mann, which is incorporated herein by reference in its entirety. The control system 30 may also be a state logic-based system such for example as that disclosed in commonly assigned U.S. Pat. No. 4,944,298 of Sholder, which is also incorporated herein by reference in its entirety. The control system 30 includes a timing circuit 37 comprised of a real-time clock, for providing timing functionality for monitoring cardiac events and for timing the application of therapeutic pulses by the pulse generators 22 and 24. The control system 30 also includes a sampler 35, such as an A/D converter, for generating digital signals representative of cardiac activity, by sampling the atrial and/or ventricular cardiac signals acquired by the respective amplifiers 26 and 28. Alternately, the sampler 35 may be implemented separately from the control system 30 and connected directly to the amplifiers 26 and 28.

The pacemaker 10 also includes a memory 44 which is coupled to the control system 30. The memory 44 allows certain control parameters used by the control system 30 in controlling the operation of the pacemaker 10 to be programmably stored and modified, as required, to customize the operation of the pacemaker 10 to suit the needs of a particular patient. In particular, parameters regulating the operation of the sampler 35 are stored in the memory 44. In addition, samples acquired by the sampler 35 may be stored in the memory 44 for later analysis by the control system 30.

The control system 30 receives the output signals from the atrial sense amplifier 26. Similarly, the control system 30 also receives the output signals from the ventricular sense amplifier 28. These various output signals are generated each time that an atrial event (e.g. a P-wave) or a ventricular event (e.g. an R-wave, far-field R-wave (FFR), or a far-field T-wave (FFT) is sensed within the heart 12.

The control system 30 also generates an atrial trigger signal that is sent to the atrial pulse generator 22, and a ventricular trigger signal that is sent to the ventricular pulse generator 24. These trigger signals are generated each time that a stimulation pulse is to be generated by one of the pulse generators 22 or 24. The atrial stimulation pulse is referred to as the "A-pulse", and the ventricular stimulation pulse is referred to as the "V-pulse". The characteristics of these stimulation pulses are determined by pacing energy settings that are among the parameters stored in the memory 44. The control system 30 may also be programmed to operate the pacemaker 10 in a variety of pacing and sensing modes. A telemetry circuit 48 is further included in the pacemaker 10, and is connected to the control system 30. The telemetry circuit 48 may be selectively coupled to an external programmer 52 by means of an appropriate communication link 54, such as an electromagnetic telemetry link or a remote communication link such as a pair of modems interconnected via a telecommunications link and equipped with telemetry capabilities.

The operation of the pacemaker 10 is generally controlled by a control program stored in the memory 44 and executed by the control system 30. This control program is typically comprised of multiple integrated program modules, with each module bearing responsibility for controlling one or more functions of the pacemaker 10. For example, one program module may control the delivery of stimulating pulses to the heart 12, while another may control the verification of ventricular capture and ventricular pacing energy determination. In effect, each program module is a control program dedicated to a specific function or set of functions of the pacemaker 10.

Figure 2A:
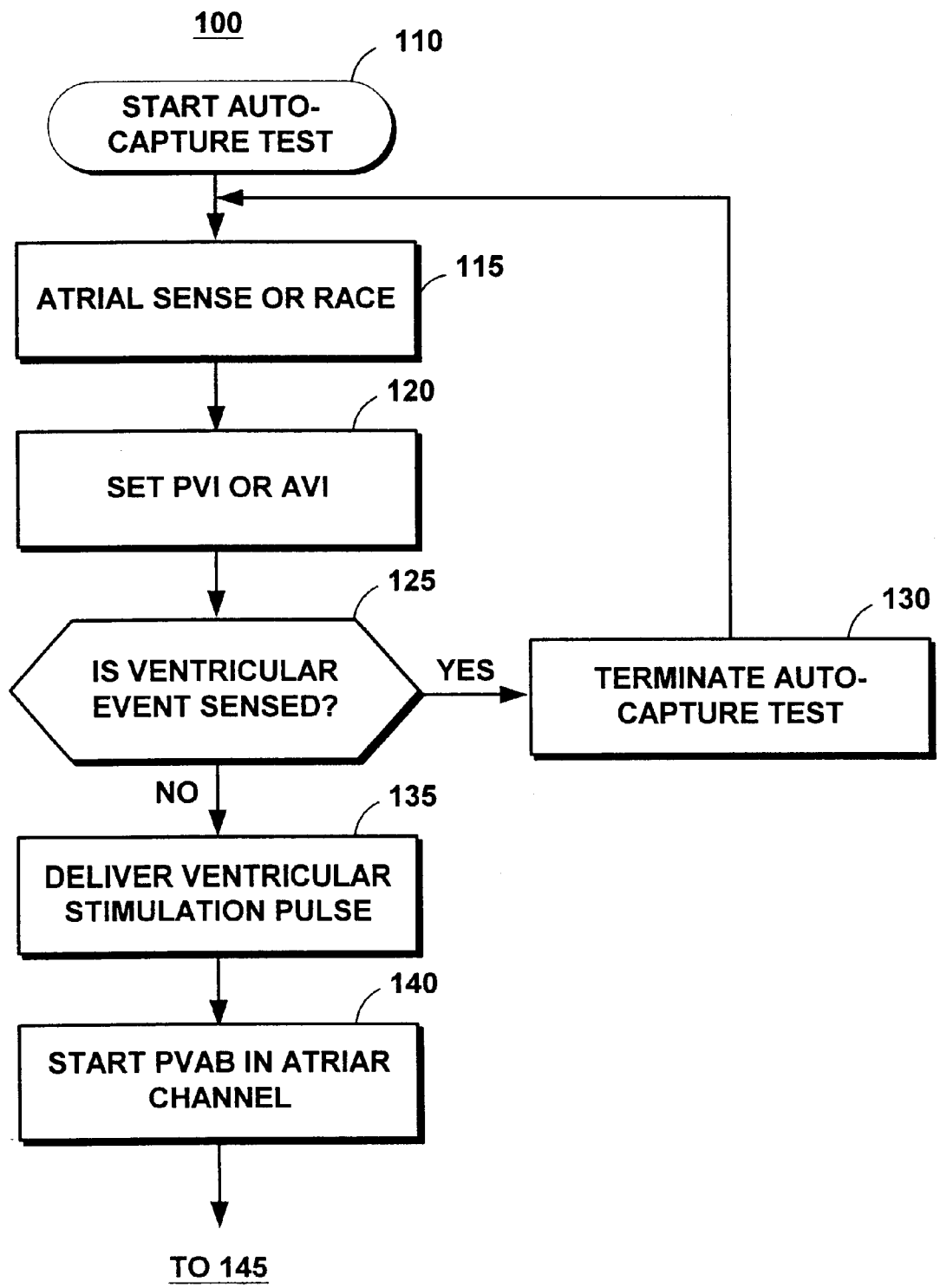
FIG. 2 is comprised of FIG. 2A and FIG. 2B, and is a logic flow diagram of an automatic ventricular capture verification control program executed by a control system of the pacemaker of FIG. 1, in accordance with the principles of the present invention.
Figure 2B:
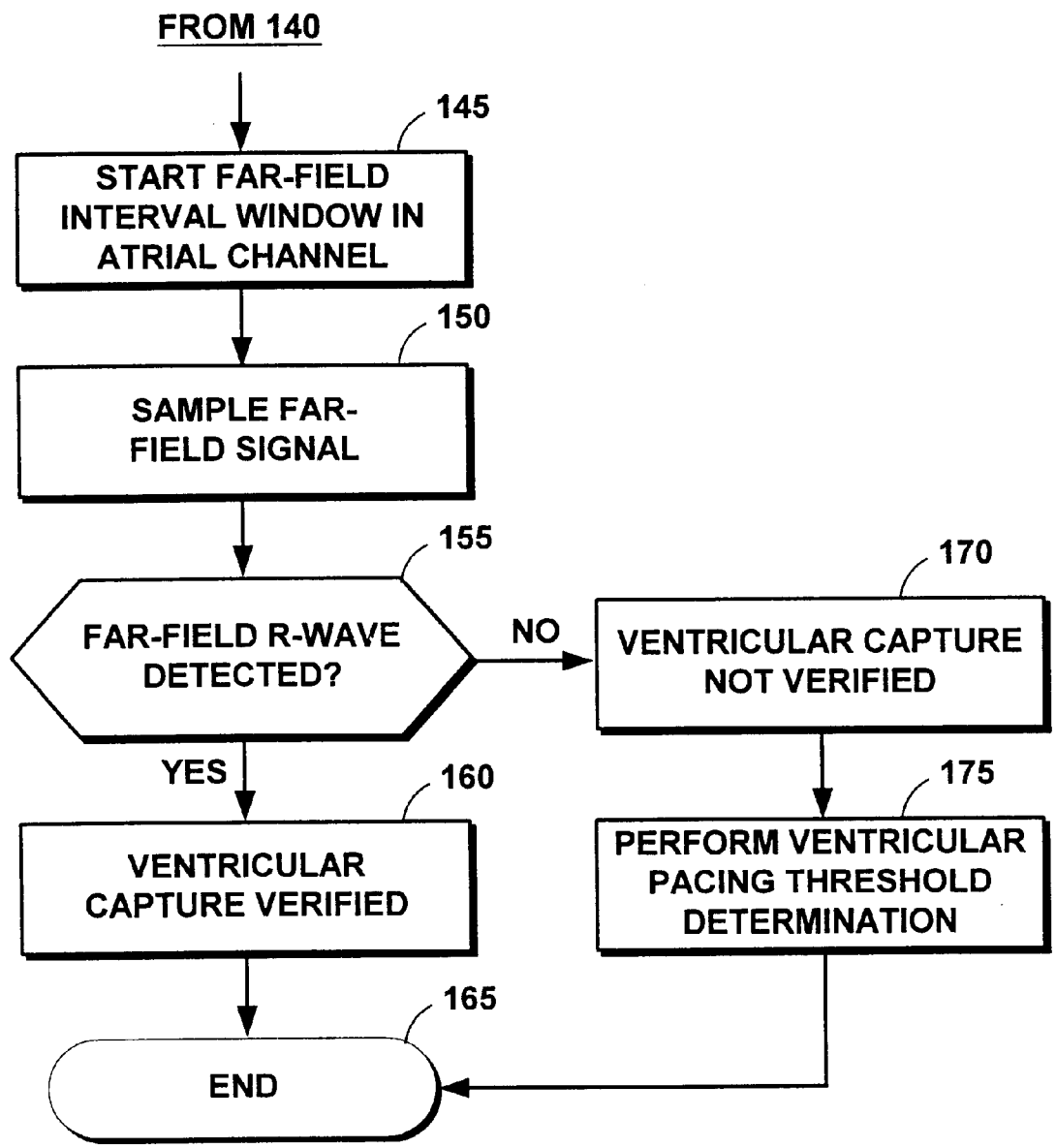

FIG. 2 (FIGS. 2A and 2B) depicts a logic flow diagram representing the operation of the control program for controlling the ventricular capture verification executed by the control system 30 in accordance with the present invention. Preferably, the control system 30 periodically invokes the control program to perform the capture verification test. The frequency with which this test is performed is preferably controlled by programmable parameters set by the medical practitioner using the external programmer 52 when the patient is examined during an office visit or remotely via the communication link 112. The appropriate testing frequency parameter will vary from patient to patient, and will depend on a number of physiologic and other factors. For example, if a patient is on a cardiac medication regimen, the patient's ventricular capture threshold may fluctuate, thus requiring relatively frequent testing.

Figure 3:
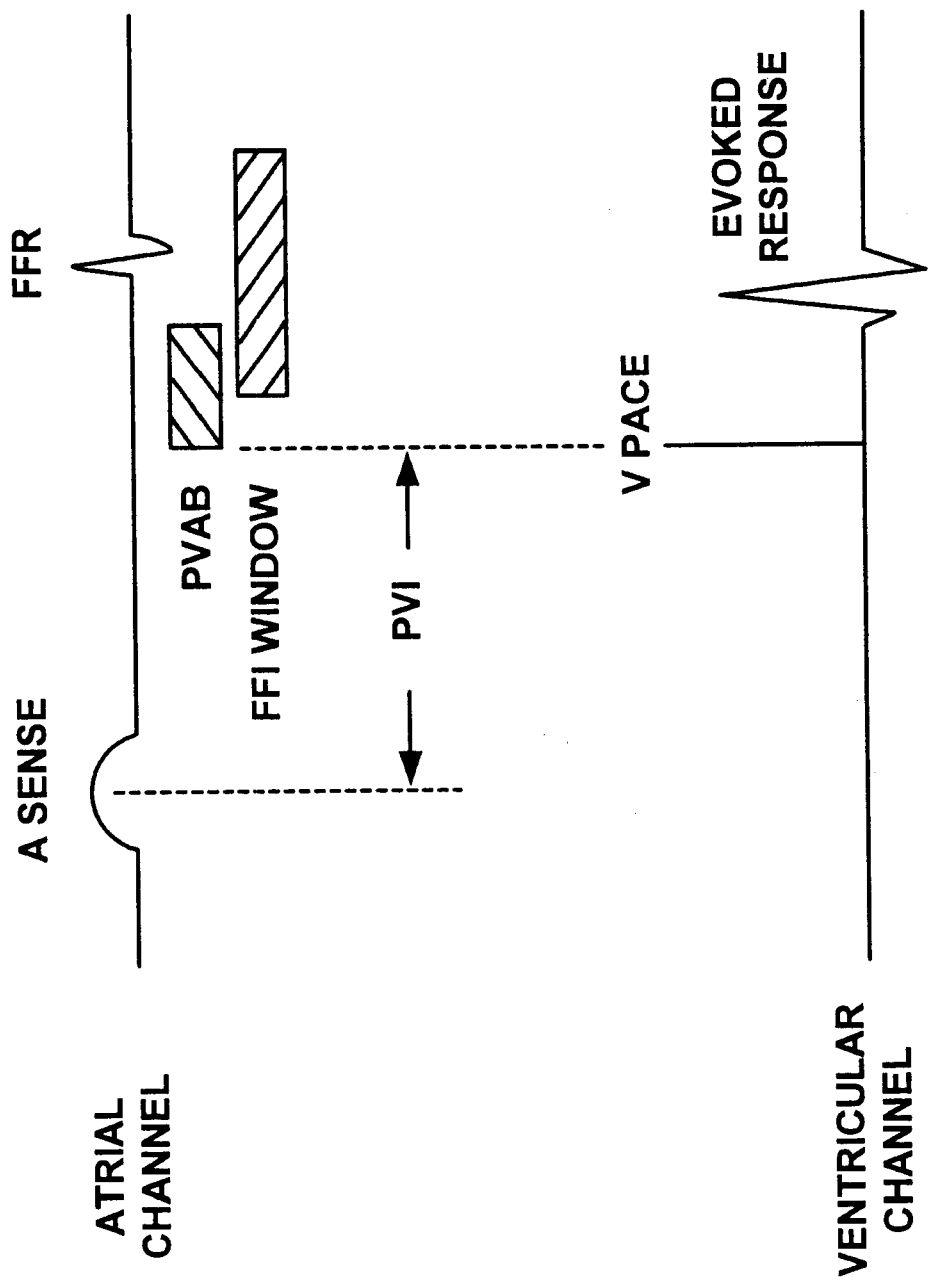
FIG. 3 is a timing diagram of an atrial channel and a ventricular channel illustrating the ventricular capture verification process of FIG. 2, through detection of a far-field R-wave (FFR) within a far-field interval (FFI) window.

FIG. 2 illustrates a ventricular autocapture verification method 100 which is implemented by the control system 30. The ventricular capture verification test begins at a step 110. With further reference to FIG. 3, and following an atrial sensed event (P-wave) at step 115 (FIG. 2A), the control system 30 sets a PV interval (PVI) at step 120. If at step 115 the control system 30 causes the atrial pulse generator 22 to deliver a stimulation pulse to the atrial chamber, the control system 30 sets an AV interval (AVI) rather than a PVI at step 120. Both the AVI and the PVI can be programmable and can range, for example, between 25 msec and 250 msec.

At decision step 125 the method 100 inquires if a ventricular event (R-wave) is sensed. If a ventricular event is sensed, the method 100 terminates the autocapture test at step 130, and returns to step 115 where it awaits for the next atrial event.

If, however, a ventricular event is not sensed at step 125, the control system 30 causes the ventricular pulse generator 24 to deliver a stimulation pulse to the ventricular chamber at step 135. Typically, the ventricular stimulation pulse triggers a subsequent ventricular contraction resulting in a ventricular evoked response that propagates to, and is sensed by the atrial sense amplifier 26 through the atrial lead 14 as a far-field signal. This far-field signal is denoted by the designation FFR. The lack of a ventricular contraction subsequent to the delivery of the ventricular stimulation pulse commonly indicates absence of ventricular capture.

The delivery of the ventricular stimulation pulse at step 135 initiates a post ventricular atrial blanking period ("PVAB") on the atrial channel (FIG. 3) at step 140, as is well recognized in the field. The PVAB can range, for example, between 50 msec and 250 msec.

After a predetermined delay period of, for example 15 msec, from the delivery of the ventricular stimulation pulse at step 135, the control system 30 sets a far-field interval (FFI) window at step 145 (FIG. 2B). According to one embodiment, the FFI window ranges between approximately 50 msec and 150 msec, and is preferably about 100 msec. The purpose of the FFI window is thus to provide an opportunity for the control system 30 to sense the far-field signal that occurs in response to the ventricular stimulation pulse.

During the FFI window, the sampler 35 of the control system 30 samples the far-field signal sensed by the atrial sense amplifier 26, at step 150, to determine its amplitude and to ascertain that it is in fact a FFR signal. To this end, the control system 30 compares the far-field signal sample obtained at step 150 with a far-field signal recognition template ("FFS template") stored in the memory 44, to determine whether the far-field signal sample is approximately equal to the FFS template. The FFS template is preferably representative of morphology of a typical FFR that occurs in the patient's heart 12.

The FFS template may be supplied by the medical practitioner using the programmer 52 or, preferably, may be automatically determined by the control system 30. The control program module described below in connection with FIG. 4 demonstrates a technique for automatically determining the FFS template.

If the control system 30 determines at decision step 155 that the far-field signal sample is approximately equal to the FFS template, it verifies ventricular capture (step 160), and the control program ends at step 165. If, however, the far-field signal sample is not approximately equal to the FFS template, the control system 30 does not verify ventricular capture (step 170), performs a ventricular pacing energy determination procedure at step 175, and the control program ends at step 165. Various advantageous and appropriate ventricular pacing energy determination procedures are well known in the art and will not therefore be described herein.

Figure 4A:
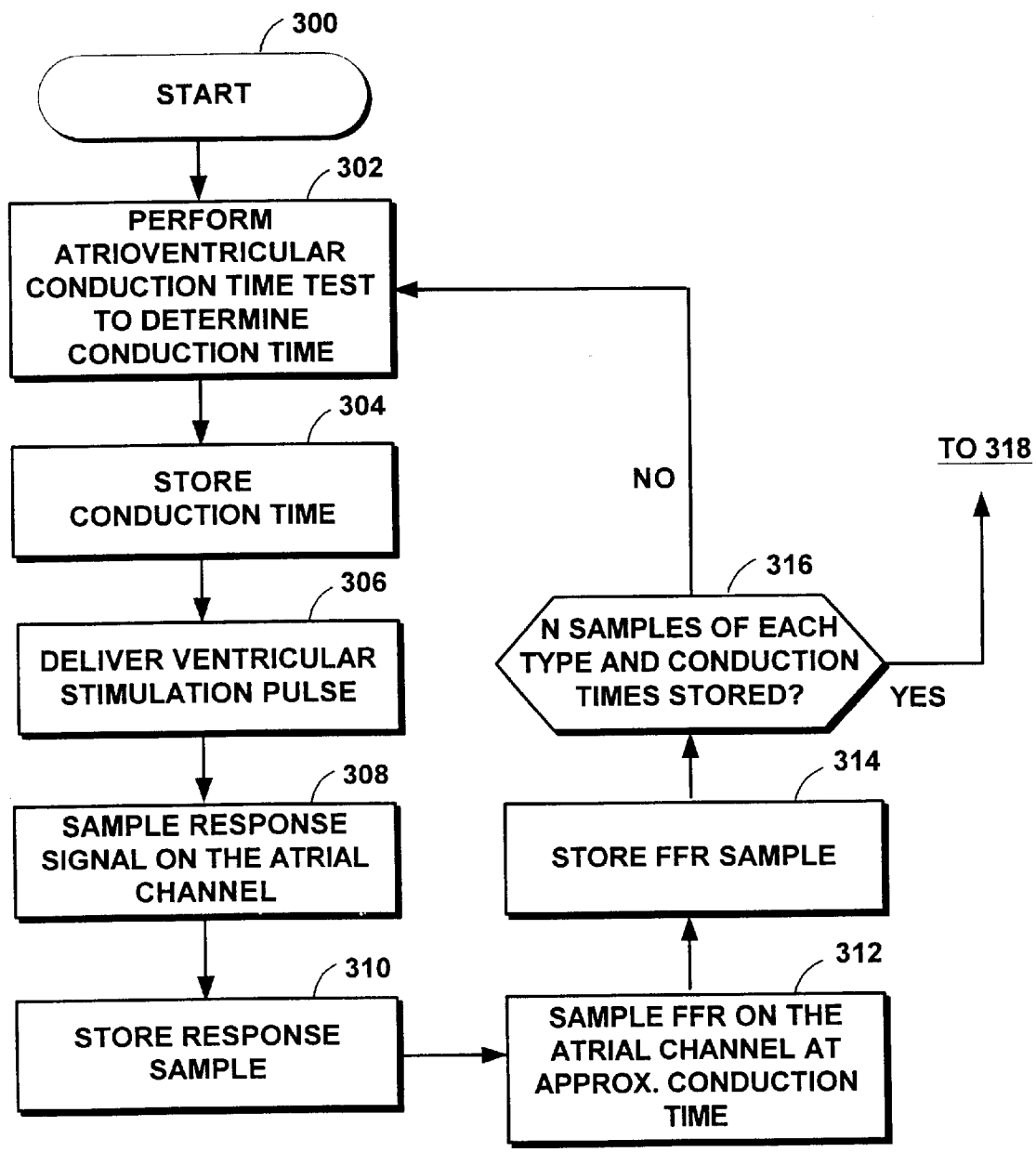
FIG. 4 is comprised of FIG. 4A and FIG. 4B, and is a logic flow diagram of an automatic far-field signal recognition template determination program executed by the control system of the pacemaker of FIG. 1, in accordance with the principles of the present invention.
Figure 4B:
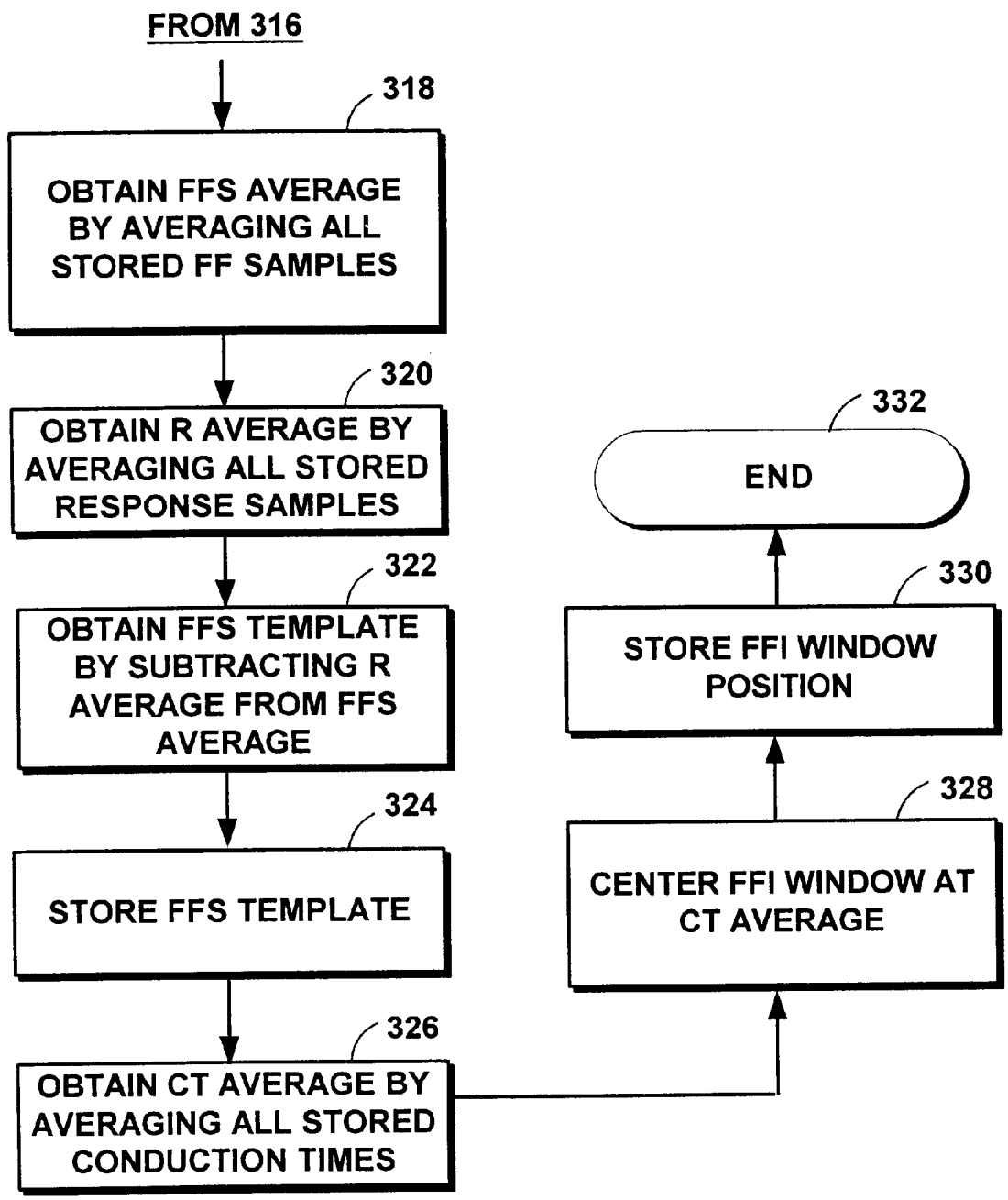

FIG. 4 depicts a logic flow diagram representing a preferred embodiment of a control program module within the control system 30, for automatically determining the FFS template. After the control program module begins at step 300, the control system 30 at step 302 performs an atrio-ventricular ("VA") conduction test to determine the expected delay ("conduction time") between the delivery of the ventricular stimulation pulse and the sensing of the far-field R-wave signal by the atrial sense amplifier 26. The expected delay is equivalent to VA conduction time. Various appropriate VA conduction time measurement procedures are well known in the art and will not therefore be described herein. At step 304 the control system 30 stores the conduction time determined at step 302 in the memory 44.

At step 306, the control system 30 causes the ventricular pulse generator 24 to deliver a stimulation pulse to the ventricular chamber of the heart 12. When delivered, the ventricular stimulation pulse triggers a ventricular pace response signal ("response signal") in the ventricular chamber that may include an evoked response representative of a ventricular contraction combined with a polarization signal. Typically, the ventricular stimulation pulse also triggers a subsequent ventricular contraction resulting in a ventricular R-wave evoked response that is sensed by the atrial sense amplifier 26 through the atrial lead 14 as a far-field (FFR) signal.

At step 308 the control system 30 samples the response signal via the sampler 35, and at a step 310 stores the response sample in the memory 44. At step 312, the control system 30 samples the FFR signal via the sampler 35 after a predetermined delay following the delivery of the ventricular stimulation pulse at step 306, approximately equal to the VA conduction time determined at step 302. At step 314 the control system 30 stores the FFR signal sample in the memory 44.

At decision step 316 the control system 30 inquires whether a predetermined number (hereinafter "N") of each of the samples (steps 310 and 314), and conduction times (step 304) are stored in the memory 44. The parameter N may be selected by the medical practitioner using the programmer 52. In order to improve the accuracy of the FFS template, N should be set to a sufficient number of samples to accurately classify the conduction time (e.g., three samples or more).

If N conduction times, response samples, and FFR samples have not been stored, then the control system 30 returns from step 316 to step 302 to perform the VA conduction test. Thus, the control system 30 repeats steps 302 through 316 until N conduction times (step 304) and N samples of each sample type (steps 310, 314) have been stored in the memory 44.

When N conduction times and N samples of each sample type have been stored, then the control system 30 determines at step 318 a FFS average representative of an average FFR sample by averaging all of the stored FFR samples (step 314, and optionally stores the FFS average in the memory 44. At step 320, the control system 30 similarly determines a R-average representative of an average response sample by averaging all of the stored response samples (step 310), and optionally stores the calculated R-average in the memory 44.

At step 322 the control system 30 determines the FFS template representative of a true far-field signal by subtracting R-average from FFS-average. Because FFS-average represents the average far-field signal whereas the raw detected far-field signal may be mixed with the response signal, subtracting R-average which is representative of just the response signal including polarization and other noise from the FFS-average results in a representation of the true far-field signal. At step 324 the FFS template is stored in the memory 44, so that it is available for future identification of a far-field signal during ventricular capture verification as described above in connection with FIGS. 2–3.

At step 326 the control system 30 determines an average expected delay value CT-average by averaging all conduction times stored in the memory 44 and, at step 328, centers the FFI window at the CT-average. At step 330 the control system 30 stores the FFI window position to increase the capability of the atrial sense amplifier 26 to sense far-field signals, and then ends the control program module at step 332.

One skilled in the art will appreciate that the present invention can be practiced by other than the described embodiments, which are presented for purposes of illustration and not of limitation.

What is claimed is:

1. A system for automatically detecting capture in a ventricular chamber of a patient's heart comprising:
   a pulse generator for generating a stimulation pulse for delivery to the ventricular chamber to trigger an evoked response so as to produce a ventricular far-field signal that follows a successfully captured ventricular stimulation pulse;
   a control system for setting a far-field interval window on an atrial channel, wherein the interval window starts a predetermined amount of time after delivery of the ventricular stimulation pulse; and
   an atrial sense circuit for sensing the ventricular far-field signal within the far-field interval window to determine ventricular capture.

2. The system according to claim 1 being implemented in a cardiac device, and wherein the cardiac device includes an atrial lead for coupling to the patient's atrial chamber, and a ventricular lead for coupling to the patient's ventricular chamber.

3. The system according to claim 2, wherein the cardiac device is a dual-chamber pacemaker.

4. The system according to claim 2, wherein the cardiac device is any one of: a pacemaker, a defibrillator, a cardioverter, or an implantable cardioverter-defibrillator.

5. The system according to claim 1, wherein the control system includes timing circuitry for providing timing functionality to monitor cardiac events and to time the application of the stimulation pulse.

6. The system according to claim 5, wherein the control system further includes a sampler for generating digital signals representative of cardiac activity, by sampling signals sensed in the atrial chamber.

7. The system according to claim 1, wherein the control system sets the far-field interval window after a predetermined delay period from the delivery of the stimulation pulse to the ventricular chamber, so as to provide an opportunity for the control system to sense the far-field signal that occurs in response to the stimulation pulse.

8. The system according to claim 7, wherein the delay period is approximately 15 msec.

9. The system according to claim 7, wherein the far-field interval window ranges between approximately 50 msec and 150 msec.

10. The system according to claim 9, wherein the far-field interval window is approximately 10 msec.

11. The system according to claim 6, wherein the sampler samples the far-field signal.

12. The system according to claim 1, wherein the delivery of the stimulation pulse initiates a post ventricular atrial blanking period on the atrial channel; and wherein the control system initiates the far-field interval window after a predetermined delay period from the delivery of the stimulation pulse.

13. The system according to claim 12, wherein the delay period is approximately 15 msec.

14. The system according to claim 12, wherein the control system initiates the far-field interval window during the post ventricular atrial blanking period.

15. A cardiac device for automatically detecting capture in a ventricular chamber of a patient's heart, comprising:

a pulse generator for generating a stimulation pulse for delivery to the ventricular chamber to trigger an evoked response so as to produce a ventricular far-field signal that follows a successfully captured ventricular stimulation pulse;

a control system for setting a far-field interval window on an atrial channel, wherein the interval window starts a predetermined amount of time after delivery of the ventricular stimulation pulse; and an atrial sense circuit for sensing the ventricular far-field signal within the far-field interval window to determine ventricular capture.

16. The cardiac device according to claim 15, wherein the control system includes a timing circuit for providing timing functionality to monitor cardiac events and to time the application of the stimulation pulse.

17. The cardiac device according to claim 16, wherein the control system sets the far-field interval window after a predetermined delay period from the delivery of the stimulation pulse to the ventricular chamber, so as to provide an opportunity for the control system to sense the far-field signal that occurs in response to the stimulation pulse.

18. The cardiac device according to claim 17, wherein the delay period is approximately 15 msec.

19. The cardiac device according to claim 17, wherein the far-field interval window ranges between approximately 50 msec and 150 msec.

20. The cardiac device according to claim 15, wherein the delivery of the stimulation pulse initiates a post ventricular atrial blanking period on the atrial channel; and wherein the control system initiates the far-field interval window after a predetermined delay period from the delivery of the stimulation pulse.

21. The cardiac device according to claim 20, wherein the delay period is approximately 15 msec.

22. The cardiac device according to claim 20, wherein the control system initiates the far-field interval window during the post ventricular atrial blanking period.

23. A method for automatically detecting capture in a ventricular chamber of a patient's heart, comprising:

delivering a stimulation pulse to the ventricular chamber to trigger an evoked response so as to produce a ventricular far-field signal that follows a successfully captured ventricular stimulation pulse;

setting a far-field interval window on an atrial channel to start a predetermined amount of time after delivering the stimulation pulse to the ventricular chamber; and sensing the ventricular far-field signal within the far-field interval window to determine ventricular capture.

24. The method according to claim 23, wherein setting the far-field interval includes setting the far-field interval window after a predetermined delay period from the delivery of the stimulation pulse to the ventricular chamber, so as to provide an opportunity for the control system to sense the far-field signal that occurs in response to the stimulation pulse.

25. The method according to claim 24, further including setting the delay period to approximately 15 msec.

26. The method according to claim 24, further including setting the delay period between approximately 50 msec and 150 msec.

27. The method according to claim 24, wherein delivering the stimulation pulse initiates a post ventricular atrial blanking period on the atrial channel.

28. The method according to claim 27, wherein setting the far-field interval window includes initiating the far-field interval window after a predetermined delay period from the delivery of the stimulation pulse.

29. The method according to claim 28, wherein initiating the far-field interval window including initiating the far-field interval window after approximately 15 msec from the delivery of the stimulation pulse.

30. The method according to claim 28, wherein initiating the far-field interval window including initiating the far-field interval window during the post ventricular atrial blanking period.

* * * * *